(12) United States Patent
Sato et al.

(10) Patent No.: US 6,368,808 B2
(45) Date of Patent: Apr. 9, 2002

(54) DNA CHIP AND ITS PREPARATION

(75) Inventors: Tadahisa Sato; Koki Nakamura, both of Kanagawa; Hiroshi Shinoki, Saitama, all of (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 09/749,146

(22) Filed: Dec. 27, 2000

(30) Foreign Application Priority Data

Dec. 27, 1999 (JP) ............................... 11-370180

(51) Int. Cl.[7] .................... C12Q 1/68; C07H 19/00; C07H 21/02; C01B 35/10; C01B 15/12
(52) U.S. Cl. .................... 435/6; 536/22.1; 536/25.3; 423/277; 423/282
(58) Field of Search .................... 435/6; 536/22.1, 536/25.3; 423/277, 282

(56) References Cited

U.S. PATENT DOCUMENTS 5,620,850 A * 4/1997 Bamdad et al. ............ 530/300

* cited by examiner

*Primary Examiner*—Jezia Riley
(74) *Attorney, Agent, or Firm*—Reed Smith LLP

(57) ABSTRACT

An analytical element (typically DNA chip) composed of a solid carrier and a group of nucleotide derivatives or their analogues fixed to the solid carrier via covalent bonding is favorably produced by a method of bringing in a liquid phase a group of nucleotide derivatives or their analogues having a reactive group at one end thereof or its vicinity into contact with a solid carrier having thereon a reactive group in the presence of a transition metal-containing catalyst.

12 Claims, No Drawings

DNA CHIP AND ITS PREPARATION

FIELD OF THE INVENTION

This invention relates to a solid carrier to which nucleotide derivatives or their analogues (e.g., oligonucleotides, polynucleotides, and peptide-nucleotides) are attached, which is generally named DNA chip and which is favorably employable for detecting, with high sensitivity, complementary nucleic acid fragments.

BACKGROUND OF THE INVENTION

Detection of a nucleic acid fragment is generally performed using a probe oligonucleotide which is complementary to the nucleic acid fragment to be detected, by way of hybridization. The probe oligonucleotide is generally fixed onto a solid carrier (e.g., solid substrate) to produce a so-called Dk chip. In the detection procedures, a nucleic acid fragment in a sample liquid is provided with a fluorescent label or a radioisotope label, and then the sample liquid is brought into contact with the probe oligonucleotide of the DNA chip. If the labelled nucleic acid fragment in the sample liquid is complementary to the probe oligonucleotide, the labelled nucleic acid fragment is combined with the probe oligonucleotide by hybridization. The labelled nucleic acid fragment fixed to the DNA chip by hybridization with the probe oligonucleotide is then detected by an appropriate detection method such as fluorometry or autoradiography. The DNA chip is widely employed in the gene technology, for instance, for detecting a complementary nucleic acid fragment and sequencing the detected nucleic acid fragment.

The DNA chip can be utilized to efficiently detect a large number of complementary nucleic acid fragments in a small amount of a sample liquid within a short period of time.

Detection of nucleic acid fragment using an electrochemical label is also known (Japanese Patent Provisional Publication No. 9-288080, and a preprint of the 57th Analytical Chemistry Conference pp. 137–138 (1996)).

P. E. Nielsen et al., Science, 254, 1497–1500(1991) and P. E. Nielsen et al., Biochemistry, 36, pp.5072–5077(1997) describe PNA (Peptide Nucleic Acid or Polyamide Nucleic Acid) which has no negative charge and functions in the same manner as DNA fragment does. PNA has a polyamide skeleton of N-(2-aminoethyl)glycine units and has neither glucose units nor phosphate groups.

Since PNA is electrically neutral and is not charged in the absence of an electrolytic salt, PNA is able to hybridize with a complementary nucleic acid fragment to form a hybrid which is more stable than the hybrid structure given by a probe oligonucleotide and its complementary nucleic acid fragment (Preprint of the 74th Spring Conference of Japan Chemical Society, pp. 1287, reported by Naomi Sugimoto).

Japanese Patent Provisional Publication No.11-332595 describes a PNA probe fixed onto a solid carrier at its one end and a detection method utilizing the PNA probe. The PNA probe is fixed onto the solid carrier by the known combination of avidin and biotin.

The aforementioned P. E. Nielsen et al., Science, 254, 1497–1500(1991) also describes a PNA probe labelled with an isotope element and a detection method of a complementary nucleic acid fragment.

Since the PNA probe shows no electric repulsion to a target nucleic acid fragment in a sample liquid, an improved high detection sensitivity is expected.

At present, two methods are known for preparing a DNA chip having a solid carrier and oligonucleotides or polynucleotides fixed onto the carrier. One preparation method comprises preparing oligonucleotides or polynucleotides, step by step on the carrier. This method is named "on-chip method". A typical on-chip method is described in Foder, S.P.A., Science, 251, page 767 (1991).

Another preparation method comprises fixing separately prepared oligonucleotides or polynucleotides onto a solid carrier. Various methods are known for various oligonucleotides and polynucleotides.

In the case of the complementary nucleotide derivatives (which are synthesized using mRNA as mold) or PCR products (which are DN fragments prepared by multiplying cDNA by PCR method), an aqeous solution of the prepared DNA fragment is spotted onto a solid carrier having a poly-cationic coat in a Dak chip-preparing device to fix the DNA fragment to the carrier via electrostatic bonding, and then blocking a free surface of the polycationic coat.

In the case that the oligonucleotides are synthetically prepared and have a functional group, an aqueous solution of the synthetic oligonucleotides is spotted onto an activated or reactive solid carrier to produce covalent bonding between the oligonucleotides and the carrier surface. See Lamture, J. B., et al., Nucl. Acids Res., 22, 2121–2125, 1994, and Guo, Z., et al., Nucl. Acids Res., 22, 5456–5465, 1994. Generally, the oligonucleotides are covalently bonded to the surface activated carrier via linking groups.

Also known is a process comprising the steps of aligning small polyacrylamide gels on a glass plate and fixing synthetic oligonucleotides onto the glass plate by making a covalent bond between the polyacrylamide and the oligonucleotide (Yershov, G., et al., Proc. Natl. Acad. Sci. USA, 94, 4913(1996)). Sosnowski, R. G., et al., Proc. Natl. Acad. Sci. USA, 94, 1119–1123 (1997) discloses a process comprising the steps of placing an array of microelectrodes on a silica chip, forming on the microelectrode a streptoavidin-comprising agarose layer, and attaching biotin-modified DNA fragments to the agarose layer by positively charging the agarose layer. Schena, M., et al., Proc. Natl. Acad. Sci. USA, 93, 10614–10619 (1996) teaches a process comprising the steps of preparing a suspension of an amino group-modified PCR product in SSC (i.e., standard sodium chloride-citric acid buffer solution), spotting the suspension onto a slide glass, incubating the spotted glass slide, treating the incubated slide glass with sodium borohydride, and heating thus treated slide glass.

As is explained above, most of the known methods of fixing separately prepared DNA fragments onto a solid carrier utilize the electrostatic bonding or the covalent bonding such as described above.

In any DNA chips hatfing separately prepared oligonucleotide probes on its solid carrier, the oligonucleotide probes should be firmly fixed onto the carrier, so that the hybridization can proceed smoothly between the fixed oligonucleotide probes and target DNA fragments complementary to the fixed oligonucleotide probes.

Further, it is preferred that a surface area of the solid carrier other than the portion to which the probe oligonucleotides are fixed is inactive to the labelled DNA fragments, so that non-complementary DNA fragments in the liquid sample can be kept from attaching onto the surface in the course of the detection procedure utilizing hybridization and kept from remaining on the surface of the carrier. If the non-complementary DNA fragments remain in the surface of the carrier, the accuracy of the detection decreases.

U.S. Pat. No. 5,387,505 describes a method of separating a target DNA fragment by binding target DNA fragments labelled with a biotin molecule with a substrate having avidin molecules.

U.S. Pat. No. 5,094,962 discloses a detection tool for a ligand-receptor assay in which receptor molecules are bonded to a porous polymer particle having a reactive group.

SUMMARY OF THE INVENTION

It is an object of the present invention to provide a solid carrier to which a group of nucleotide derivatives or their analogues (e.g., oligonucleotides, polynucleotides, and peptide-nucleotides, which serve as probes for detecting complementary DNA fragments by way of hybridization) are attached and which is favorably employable for detecting, with high sensitivity, complementary nucleic acid fragments.

It is another object of the invention to provide a DNA chip which is employable in the procedure for detecting complementary DNA fragments without performing in advance a blocking procedure, that is, a procedure of inactivating the solid carrier in the areas having no probes, so as to keep non-complementary DNA fragments from fixing on the carrier by non-hybridization mechanism.

The present invention resides in an element comprising a solid carrier and a group of nucleotide derivatives or their analogues which are fixed to the solid carrier via covalent bonding, in which the covalent bonding is produced by a reaction between a reactive group attached to the solid carrier and a reactive group attached to the nucleotide derivative or analogue in the presence of a transition metal-containing catalyst.

The invention also resides in a method for preparing an element comprising a solid carrier and a group of nucleotide derivatives or their analogues fixed to the solid carrier via covalent bonding which comprises bringing in a liquid phase a group of nucleotide derivatives or their analogues having a reactive group at one end thereof or its vicinity into contact with a solid carrier having thereon a reactive group in the presence of a transition metal-containing catalyst.

In the invention, the transition metal contained in the catalyst preferably is scandium, cobalt, nickel, copper, ruthenium, rhodium, palladium, or one of lanthanids. The reactive group attached to the solid carrier or the reactive group attached to the nucleotide derivative or analogue preferably contains a double bond or a triple bond, preferably, at its terminal.

A preferred combination resides in that the transition metal-containing catalyst is a palladium-containing catalyst, and one of the reactive group attached to the solid carrier or the reactive group attached to the nucleotide derivative or analogue is a residue of an alkylboronic acid, an alkenylboronic acid, or an arylboronic acid and another is a residue of an alkenyl halide or an aryl halide.

Another preferred combination resides in that the transition metal-containing catalyst is a palladium-containing catalyst, and one of the reactive group attached to the solid carrier or the reactive group attached to the nucleotide derivative or analogue is a residue of an alkenyl halide or an aryl halide and another is a terminal alkyne group.

The detection method of the invention for oligonucleotides or polynucleotides such as DNA fragments can be performed by bringing the solid carrier having probes (i.e., a group of nucleotide derivatives or their analogues) fixed onto its surface into contact with oligonucleotides or polynucleotides (such as target DNA fragments) which are complementary to the probes of nucleotide derivatives or their analogues fixed onto the surface of the solid carrier in the presence of an aqueous solvent, so as to combine the complementary oligonucleotides or polynucleotides with the nucleotide derivatives or their analogues. It is preferred that the probe compound has a double bond or triple bond at its terminal.

DETAILED DESCRIPTION OF THE INVENTION

Solid Carrier

The solid carrier can be any of known solid carriers or their equivalent materials, for instance, a glass plate, a resin plate, a metal plate, a glass plate covered with polymer coat, a glass plate covered with metal coat, and a resin plate covered with metal coat. Also employable is a SPR (surface plasmon resonance) sensor plate which is described in Japanese Patent Provisional Publication No. 11-332595. CCD is also employable as described in Nucleic Acids Research, 1994, Vol.22, No.11, 2124–2125.

Probe Compound—Nucleotide Derivative or Its Analogue

The probe compounds, namely, nucleotide derivatives or their analogues to be fixed to the solid carrier can be oligonucleotides, polynucleotides, or peptide-nucleotides. A DNA fragment can be employed as the probe compound.

The nucleotide derivative may be polynucleotide such as cDNA, a portion of cDNA, or EST. The polynucleotide is favorably employed for studying gene expression. Otherwise, nucleotide derivatives to be fixed onto the solid carrier may be oligonucleotides, which are favorably employed for studying variations and polymorphism of gene. The oligonucleotide to be fixed onto the solid carrier preferably is one of 3 to 50-mers, more preferably 10 to 25 mers. The oligonucleotide and polynucleotide can have one or more substituent groups and/or cross-linking groups, provided that the attachment of these groups does not impart adverse influence to the function of the oligonucleotide and polynucleotide. For instance, LNA (locked nucleic acid) which is described in J. Am. Chem. Soc., 1998, 120, 13252–13253, can be employed.

Reactive Groups—Attached to Solid Carrier or Probe Compound

The characteristic feature of the invention resides in producing a covalent bond between the solid carrier and the probe compound by a reaction between a reactive group attached to the solid carrier and a reactive group attached to the probe compound in a liquid phase in the presence of a transition metal-containing catalyst.

The general descriptions on the reactions for the production of covalent bonding in the presence of a transition metal-containing catalyst are set forth in Akio Yamamoto, "Organic Metal Chemistry", Shokabo 1982, Hiroshi Yamazaki, Yasuo Wakatsuki, "Chemistry of Organic Metals", Dai-nippon Tosho, 1989, Koji Yamakawa, Yoshikazu Matsushima, Masao Kurume, "Chemistry of Organic Metal Complex", Kodansha 1989, Ch. Elschenbroich, A. Salzer, "Organometallics, A Concise Introduction", VCH Publishers 1989, Masatoshi Watabe, Shigenobu Yano, Takao Ikariya, "Fundamental of Complex Chemistry", Kodansha 1990, Taku Ito, Kichiro Uchimoto, Akira Nakamura, Manobu Hidai, "Chemical Reviews-17, Organic Chemistry of Former Periodical Transition Metal" edited by Hiroshi Yamazaki, Gakkai Publishing Center, 1993; Jiro Tsuji, "Organic Synthesis Developed Using Transition Metal, Its Various Reaction Modes & New Development", Kagaku Dojin Co., Ltd. 1997; L. Brandsma, S. F. Vasilevsky, H. D. Verkruijsse, "Application of Transition Metal Catalysts in Organic Synthesis" Springer, 1998; and "Organic Synthesis in Water" edited by Paul A. Grieco, Blackie Academic & Professional 1998.

Examples of the transition metal-containing catalysts employable in the reaction of fixing the probe compound onto the surface of the solid carrier include scandium, titanium, vanadium, chromium, manganese, iron, cobalt, nickel, copper, yttrium, zirconium, niobium, molybdenum, ruthenium, rhodium, palladium, silver, cadmium, lanthanid metals, hafnium, tantalum, tungsten, rhenium, osmium, iridium, platinum, gold, and mercury. Preferred are scandium, cobalt, nickel, copper, ruthenium, rhodium, palladium, and lanthanid metals (particularly, ytterbium, samarium, praseodymium, neodymium, and gadolinium). Most preferred is palladium.

Examples of combinations of the reactive groups employable for the production of covalent bonding between the solid carrier and the probe compound (i.e., nucleotide derivative or its analogue) are set forth below. Details of these combinations and other possible combinations are described in the aforementioned publications. One of the reactive group is attached to a surface of a solid carrier, and another is attached to a probe compound, namely, a nucleotide derivative or its analogue, preferably at the terminal.

(1) Palladium catalyst aryl iodide/olefin; aryl bromide/olefin; diazonium salt/olefin; carbonyl halide/olefin; enol ether/olefin; alkyl-, alkenyl- or aryl-boronic acid/aryl iodide or aryl bromide; arylboronic acid/alkenyl or aryl trifulate; Grignard reagent/aryl trifulate; diarylphosphine oxide/aryl-trifulate; arylboronic acid/diazonium salt; alkenylboronic acid ester/alkenyl bromide; heteroaryl iodide/Reformatsky reagent; alkenyl trifulate/aryl zinc reagent; aryltrifulate/heteroaryl zinc reagent; alkyl zinc reagent/alkenyl trifulate; alkylborane/alkyl iodide; alkylborane/vinyl trifulate; alkenylaluminum reagent/alkenyl iodide or aryl iodide; aryl trifulate/alkylaluminum; alkenylzirconocene reagent/alkenyl iodide; alkenyltin reagent/alkenyl iodide or aryl iodide; alkenylsilane/aryl iodide; arylsilane/aryltrifulate; alkenylsilane/aryl chloride; bis(pinacolate)diborone/aryl bromide; aryl bromide or aryl iodide/tetraaryl borate; disilane/alkenyl iodide; benzyl chloride/disilane; carbonyl chloride/disilane; malononitrile or cyanoacetic acid ester/aryl bromide or aryl iodide; aryl bromide/alkylamine or arylamine; aryliodide or aryl bromide/alkanethiol or arylthiol; aryl iodide/phosphinic acid ester; aryl bromide or aryl iodide/terminal alkyne; alkenyl chloride, alkenyl bromide or alkenyl iodide/terminal alkyne; alkene iodide/alkynyltin reagent; alkynyl iodide/terminal alkyne; aryl bromide or aryl iodide/interrnal alkyne; alkene bromide or alkene iodide/internal alkyne; aryl trifulate, aryl chloride, aryl bromide or aryl iodide/alcohol or amine/carbon monoxide (supplied from outside in the gaseous form; aryl iodide/alkylzinc reagent; alkenyl trifulate/alkenyltin reagent/carbon monoxide (supplied from outside in the gaseous form); carbonyl halide/Reformatsky reagent; enone/malonic acid ester or sulfonylacetic acid ester; arylester or aryl halide/active methylene compound such as malonic acid ester or sulfonylacetic acid ester; arylester or aryl halide/silylenol ether or enol ester of ketone; conjugated diene/conjugated diene; conjugated diene/alcohol; conjugated diene/phenol; conjugated diene/carboxylic acid; conjugated diene/primary amine or secondary amine; conjugated diene/active methylene compound; conjugated diene/nitroalkane; conjugated diene/nitroalkene; conjugated diene/enamine; conjugated diene/silane having silicon-hydrogen bonding; conjugated diene/alcohol/carbon monoxide (supplied from outside in the gaseous form); conjugated diene/disilane; carbonyl halide/conjugated diene/disilane; catechol boran/conjugated diene; alkyne/arylic acid ester; alkyne/alcohol/carbon monoxide (supplied from outside in the gaseous form), propargyl alcohol/halocarbonic acid ester; propargyl alcohol carbonate/active methylene compound; ethynyloxirane/active methylene compound; propargylmethane sulfonate/arylamine; conjugated diene/olefin; terminal olefin/alcohol/carbon monoxide (supplied from outside in the gaseous form); terminal alkyne/silane having silicon-hydrogen bonding/carbon monoxide (supplied from outside in the gaseous form); olefin/olefin; olefin/alkyne; alkyne/alkyne; terinal alkyne/terminal alkyne; aryl alcohol or its carbonic acid ester/aldehyde; aryl iodide or aryl trifulate/phosphorous acid ester; aryl iodide or aryl bromide/terminal alkyne or terminal olefin; and diaryl iodonium salt/olefin or acrylic acid.

(2) Nickel catalyst vinyl iodide/olefin; Grignard reagent/aryl bromide; arylboronic acid/aryl chloride; arylboronic acid/arylmethane sulfonate; aryl trifulate/diarylphosphine; diarylphosphine oxide/aryl trifulate/alkenyl carbamate/alkyl Grignard reagent; aryl chloride, aryl bromide or aryl iodide/aryl chloride, aryl bromide, or aryl iodide; aryl trifulate/aryl trifulate; conjugated diene/conjugated diene; alkyne/conjugated diene; conjugated diene/olefin; propiol acid ester/propiol acid ester; terminal alkyne/terminal alkyne.

(3) Iron catalyst conjugated diene/conjugated diene; alkyne/conjugated diene; conjugated diene/olefin; alkyne/alkyne.

(4) Titanium catalyst conjugated diene/olefin; ketone/ketone.

(5) Rhodium catalyst alkyne/conjugated diene; alkyne/olefin; diazo compound/olefin; diazo compound/ketone; alkyne/alkyne; alkyne/silane having silicon-hydrogen bonding.

(6) Cobalt catalyst conjugated diene/conjugated diene; conjugated diene/acrylic acid ester; alkyne/nitrile; alkyne/alkyne.

(7) Ruthenium catalyst conjugated diene/acrylamide; terminal alkyne/α, β, γ, δ-unsaturated carboxylic acid; olefin/olefin; alkyne/alkyne; alkyne/nitrile; alkyne/olefin; alkyne/isocyanate; α, β-unsaturated nitrile/α, β-unsaturated nitrile; alkyne/olefin; alkyne/isocyanate; α, β-unsaturated nitrile/α, β-unsaturated nitrile/hydrogen (supplied from outside in the gaseous form); acrylic acid ester/acrylic acid ester; alkyne/acrylic acid ester; alkyne/silane having silicon-hydrogen bonding.

(8) Platinum catalyst conjugated diene/diborane; olefin/silane having silicon-hydrogen bonding; alkyne/silane having silicon-hydrogen bonding.

(9) Tungusten catalyst olefin/olefin; olefin/ketone.

(10) Rhenium catalyst olefin/olefin.

(11) Molybdenum catalyst olefin/ketone.

(12) Copper catalyst diazo compound/olefin.

(13) Chromium catalyst gem-alkyl diiodide/aldehyde.

(14) Scandium catalyst, Lanthanid catalyst enol silyl ether/aldehyde; aryltin reagent/aldehyde; α, β-unsaturated carbonyl compound/conjugated diene; enol silyl ether/imine; enol ether/imine; imine/conjugated diene.

In the present invention, preferred combinations are as follows;

(1) the transition metal-containing catalyst is a palladium-containing catalyst, and one of the reactive group attached to the solid carrier or the reactive group attached to the nucleotide derivative or analogue is a residue of an alkylboronic acid, an alkenylboronic acid, or an arylboronic acid and another is a residue of an alkenyl halide or an aryl halide.

(2) the transition metal-containing catalyst is a palladium-containing catalyst, and one of the reactive group attached to the solid carrier or the reactive group attached to the nucleotide derivative or analogue is a residue of an alkenyl halide or an aryl halide and another is a terminal alkyne group.

In the transition metal-containing catalyst, the transition metal can be present in various oxidation states, and the oxidation state can be appropriately selected depending upon the desired reaction system, by referring to the descriptions set forth in the aforementioned publications and references listed in the publications. If the transition metal has a valency other than zero-valency, a counter anion is required. Various anions can be employed as the counter anions. Examples of the counter anions include halide ions (e.g., fluoride ion, chloride ion, bromide ion, and iodide ion), carboxylate ions (e.g., acetate ion, citrate ion, and oxalate ion), sulfonate ions (e.g., methanesulfonate ion, trifluoromethanesulfonate ion, and p-toluenesulfonate ion), sulfate ion, nitrate ion, cyclopentadienyl ion, and pentamethylcyclopentadienyl ion.

The transition metal-containing catalyst behaves differently dependent upon on its ligand molecule. Appropriate ligand molecules can be selected based on the descriptions set forth in the aforementioned publications and references listed in the publications. Examples of the appropriate ligand include acetylacetone, N,N'-bis(benzylidene) ethylendiamine, 2,2'-bis(diphenylphosphino)-1,1'-binaphthyl, [2-(diphenylphosphino-1,1'-binaphthalen-2'-yl), 1,1'-binaphthanlen-2,2'-yl]phosphine, 1,1'-bi-2-naphthol, 2,2'-bis(diphenylphosphino)-6,6'-dimethyl-1,1'-biphenyl, (2S,4S)-N-t-butoxycarbonyl-2,4-bis(diphenylphosphino) methylpyrrolidine, 2,2'-bipyridyl, 1,5,9-cyclodecatriene, 1,5-cyclooctadiene, cyclooctatetraene, dibenzylidene acetone, 1,4-diazabicyclo[2.2.2]octane, 2,3-di (cyclohexylphosphino)ethane, 2,3-o-isopropylidene-2,3-dihydroxy-1,4-bis(diphenylphosphino)butane, 1,2-bis[(o-methoxyphenyl)phenylphosphinoe]ethane, 1,2-dimethoxyethane, diphenyl(m-sulfophenyl)phosphine, bis (diphenylphosphino)ethane, bis(diphenylphosphino)butane, 1,1'-bis(diphenylphosphino)ferrocene, bis (diphenylphosphphino)propane, ethylenebis (tetrahydroindenyl), 2,2'-bis[1-(diphenylphosphino)ethyl]-1,1'-biferrocene, 1,10-phenanthroline, N,N-dimethyl-1,2-(diphenylphosphino)ferrocenylethylamine, 1,2-bis(trans-2, 5-diiscpropylphosphorano)ethane, pyridine, 4-dimethylaminopyridine, tri(2,6-dimethoxyphenyl) phosphine, tri(2-furyl)phosphine, trimethylol propanephosphite, tri(m-sulfophenyl)phosphine, N,N,N',N'-tetramethyl-1,2-ethylenediamine, tri(otolyl)phosphite, and triphenylphnosphine.

The ligand molecules can be employed singly or in combination.

The ligand molecule can be attached to the transition metal in advance with the reaction for fixing the probe compound onto the carrier, or can be added into the solution of probe compound when the solution is spotted on the carrier for fixation.

The reactive group can be attached to the probe compound such as a nucleotide derivative or its analogue by one of the following two methods.

(1) A primer which is a probe compound having a specific reactive group is multiplied by the PCR method.

(2) A primer which is a probe compound having a reactive group such as amino is multiplied by the PCR method, and to the resulting probe compounds having a reactive group is attached a specific reactive group.

Generally, the latter method can be readily performed, and accordingly is preferred in the present invention. The attachment of an amino group to the probe compound can be attained by forming an amide bonding between the amino group and a carboxyl group of an appropriate compound using an appropriate condensing agent.

Procedure of Fixing Probe Compounds

The surface of the solid carrier has reactive groups which react with the reactive group of the probe compound in the presence of a transition metal-containing catalyst. If the solid carrier has amino groups (which are produced, for instance, by bringing the surface of the solid carrier into contact with a silane-coupling agent such as 3-aminopropyltrimethoxysilane), a compound having both of a group reactive with the amino group and a group which can react with the reactive group of the probe compound in the presence of a transition metal-containing catalyst to produce covalent bonding is brought into contact with the amino groups on the surface of the solid carrier. The group reactive with the amino group, that is, a linking group, can be carboxyl, formyl, sulfo, isocyanato, isothiocyanato, and acid anhydride. A carboxyl group which can produce an amido bonding is preferred.

The solid carrier can be coated with a homopolymer or a copolymer containing a group which can react with the reactive group of the probe compound in the presence of a transition metal-containing catalyst to produce covalent bonding. The copolymer can further contain a structure corresponding to a silane coupling agent. The polymer coated on the solid carrier can be heated for fixing it firmly onto the solid carrier.

When an acrylate group or an acrylamide group is fixed onto the solid carrier, a homopolymer or copolymer having acrylate units or acrylamide units some of which remain unreacted in the polymer can be employed.

The solid carrier can be treated on its surface with a multifunctional coupling agents such as a silane coupling agent, a multifunctional epoxy compound, a multifunctional vinylsulfone, and cyanyl chloride. A silane-coupling agent is preferred. Examples of the silane-coupling agents include 1,2-bis(trimethoxysilyl)ethane, 1,7-dichlorooctamethyltetrasiloxane, 1,3-dichloro-,1,1,3,3-tetraisopropylsiloxane, and 3-glycidyloxypropyltrimethoxysilane. The solid carrier can be treated with corona discharge or coated with a hydrophilic polymer such as gelatin so as to increase adhesion between the treated surface and the coat placed on the surface.

The nucleotide derivatives (or their analogues) to be fixed on the solid carrier are dissolved or dispersed in an aqueous solution. Generally, the aqueous solution is once placed on a plastic plate having 96 or 384 wells, and then spotted onto a solid carrier using a spotting means.

The reaction for fixing the probe compounds having a reactive group preferably at their terminal (or in the vicinity) to the solid carrier having on its surface a reactive group can be performed at ambient temperatures or under cooling (such as 5 to 10° C.) or heating. The heating condition is favorably adopted. Preferably, the reaction is performed at 4 to 150° C., more preferably at 50 to 130° C., most preferably at 50 to 100° C. The reaction can be conducted in a pressure-resistant vessel such as an autoclave.

The reactions employed in the fixing the probe compounds onto the solid carrier can be preferably conducted in the presence of a base. The base can be an organic base or an inorganic base which may be employed singly or in combination. Examples of the inorganic bases include potassium carbonate, sodium carbonate, cesium carbonate, lithium hydroxide, sodium hydroxide, potassium hydroxide, cesium hydroxide, calcium hydroxide, and magnesium hydroxide. Examples of the organic bases include trimethylamine, triethylamine, tetramethylammonium hydroxide, dimethylbenzylamine, diethylaniline, pyridine, 4-dimethylaminopyridine, 1,4-diazabicyclo [2.2.2]octane, 1,8-diazabicyclo[5.4.0]-7-undecene, sodium methoxide, sodium ethoxide, potassium t-butoxide, n-butyllithium, lithium diisopropylamide, tetrabutylarnonium hydroxide, sodium acetate, and potassium acetate. The base can be employed in combination.

Alternatively, the reaction for fixation may be performed in the presence of an inorganic acid or an organic acid, such as hydrochloric acid, trifluoroacetic acid, acetic acid, sulfuric acid, or p-toluenesulfonic acid. with an acid.

The reaction for fixing can be performed in an aqueous solvent or an organic solvent. The organic solvent may be a hydrophobic solvent such as toluene, xylene or n-hexane. However, a polar solvent which is miscible with water can be preferably employed. Examples of the preferred polar solvents include ethyl acetate, methyl acetate, methanol, ethanol, isopropyl alcohol, n-butanol, t-butanol, sulforane, 1,2-diemethoxyethane, dimethylformamide, dimethylsulfoxide, dimethylacetamide, acetonitrile, propionitrile, diethyl ether, tetrahydrofuan, ethylene glycol, 1,3-propanediol, 1,4-butanediol, glycerol, 2-methoxyethanol, diethylene glycol, diethylene glycol dimethyl ether, acetic acid, pyridine, formic acid, propionic acid, and valeric acid.

In order to keep the spotted aqueous solution from evaporating, it is preferred to add a high boiling-point compound to the aqueous solution containing nucleotide derivatives. The high boiling-point compound should be soluble in an aqueous medium, should not disturb hybridization procedure, and preferably has an appropriate viscosity. Examples of the high boiling-point compounds include glycerol, ethylene glycol, dimethylsulfoxide, and a hydrophilic polymer having a low molecular weight (typically, in the range of $10^3$ to $10^6$) such as polyacrylamide, polyethylene glycol, or poly(sodium acrylate). The high boiling-point compound preferably is glycerol or ethylene glycol. The high boiling-point compound is preferably incorporated into an aqueous nucleotide derivative solution in an amount of 0.1 to 2 vol %, particularly 0.5 to 1 vol. %. Otherwise, the spotted aqueous solution is preferably kept at under the conditions of a high humidity (such as 90% RH or higher) and an ordinary temperature (25 to 50° C).

The aqueous solution is spotted onto the solid carrier under the condition that each drop of the solution generally has a volume of 100 pL to 1 μL, preferably 1 to 100 nL. The nucleotide derivatives preferably spotted onto the solid carrier are in an amount (number) of $10^2$ to $10^5/cm^2$. In terms of mol., 1 to $10^{-15}$ moles are spotted. In terms of weight, several ng or less of nucleotide derivatives are spotted. The spotting of the aqueous solution is made onto the solid carrier to form several dots having almost the same shape and size. It is important to prepare these dots to have the same shape and size, if the hybridization is quantitatively analyzed. Several dots are formed separately from each other with a distance of 1.5 mm or less, preferably 100 to 300 μm. One dot preferably has a diameter of 50 to 300 μm.

After the aqueous solution is spotted on the solid carrier, the spotted solution is preferably incubated, namely, kept for a certain period at room temperature or under warming, so as to fix the spotted nucleotide derivatives onto the carrier. In the course of incubation, UV irradiation or surface treatment using sodium borohydride or a Shiff reagent may be applied. The UV irradiation under heating is preferably adopted. It is assumed that these treatments are effective to produce additional linkage or bonding between the solid carrier and the attached oligonucleotide derivatives. The free (namely, unfixed) nucleotide derivatives are washed out using an aqueous solution. Thus washed solid carrier is then dried to give a nucleotide derivative-fixed solid carrier (such as DNA chip) of the invention.

It is not necessary to subject thus prepared analytical element to blocking treatment. However, the analytical element may be subjected to blocking treatment, if desired.

The nucleotide derivative-fixed solid carrier of the invention is favorably employable for monitoring of gene expression, sequencing of base arrangement of DNA, analysis of mutation, analysis of polymorphism, by way of hybridization.

Sample Nucleic Acid Fragment—Target

A target DNA fragment or a sample DNA fragment, which is subjected to the analysis concerning the presence of a complementary DNA fragment can be obtained from various origins. In the analysis of gene, the target DNA fragment is prepared from a cell or tissue of eucaryote. In the analysis of genome, the target DNA fragment is obtained from tissues other than erythrocyte. In the analysis of mRNA the target sample is obtained from tissues in which mRNA is expressed. If the DNA chip has an oligonucleotide fixed in its solid carrier, the target DNA fragment preferably has a low molecular weight. The target DNA may be multiplied by PCR method.

To the target DNA fragment is attached an RI label or a non-RI label by a known method. The non-RI label is preferably utilized. Examples of the non-RI labels include fluorescence label, biotin label, and chemical luminescence label. The fluorescence label is most preferably employed. Examples of the fluorescence labels include cyanine dyes (e.g., Cy3 and Cy5 belonging to Cy Dye™ series), rhodamine 6G reagent, N-acetoxy-$N^2$-acetylaminofluorene (AAF), and AAIF (iodide derivative of AAF). The target or sample DNA fragments labelled with different fluorescence indicators can be simultaneously analyzed, if the fluorescence indicators have fluorescence spectrum of different peaks. Also employable is an electroconductive label.

Hybridization

The hybridization is performed by spotting an aqueous sample solution containing a target DNA fragment onto a DNA chip. The spotting is generally done in an amount of 1 to 100 nL. The hybridization is carried out by keeping the DNA chip having the spotted sample solution thereon at a temperature between room temperature and 70° C., for 6 to 20 hours. After the hybridization is complete, the DNA chip is washed with an aqueous buffer solution containing a surface active agent, to remove a free (namely, unfixed) sample DNA fragment. The surface active agent preferably is sodium dodecyl sulfate (SDS). The buffer solution may be a citrate buffer solution, a phosphate buffer solution, a borate buffer solution, Tris buffer solution, or Goods buffer solution. The citrate buffer solution is preferably employed.

The present invention is further described by the following examples.

EXAMPLE 1

Manufacture of Oligonucleotide-Fixed Plates (1) Preparation of glass plate having on its surface terminal alkyne groups A slide glass (25 mm×75 mm) was immersed in an ethanol solution of 2 wt. % aminopropylethoxysilane (available from Shin-etsu Chemical Industries, Co., Ltd.) for 10 minutes. Subsequently, the slide glass was taken out, washed with ethanol, and dried at 110° C. for 10 min. Thus, a silane coupling agent-treated slide glass (A) was prepared.

The silane coupling agent-treated slide glass (A) was then immersed in 50 mL of a mixture of 4 wt. % of 6-heptynoic acid (available from Tokyo Kasei Co., Ltd.) and 2 wt. % of 1-ethyl-3-(3-dimethylaminopropyl)carbodiimide hydrochloride (available from Tokyo Kasei Industries, Co., Ltd.) for one hour. Subsequently, the slide glass was taken out of the solution, washed with acetonitrile, and dried for one hour under reduced pressure, to prepare a glass plate (C1) on which a group of chains having at their free terminals an alkyne moiety were fixed.

In the same manner as above except for replacing the 6-heptynoic acid with 4-carboxyphenylboronic acid (available from Tokyo Kasei Co., Ltd.), a glass plate (C2) on which a group of chains having at their free terminals an arylboronic acid moiety.

(2) Fixation of Oligonucleotide and Measurement of Fluorescence Strength

An oligonucleotide (3'-CTAGTCTGTGAAGTGTCTGATC-5', 22-mers) having an amino group at 3'-terminal and a fluorescent label (FluoroLink, Cy 5-dCTP, available from Amasham Pharmacia Biotec Corp.) at 5'-terminal was treated with 4-iodobenzoic acid and 1-ethyl-3-(3-dimethylaminopropyl) carbodiimde hydrochloride (available from Tokyo Kasei Co., Ltd.) to incorporate a 4-iodophenylcarbonylamino moiety into the 3'-terminal of the oligonucleotide.

The oligonucleotide having a 4-iodophenylcarbonylamino moiety into the 3'-terminal at its 3'-terminal was dispersed in 1 µL of an aqueous solution containing a carbonate buffer solution (0.1M, pH 9.8) at a concentration of $1 \times 10^{-6}$M. Further, to the solution was added tetrakis[tri(m-sulfophenyl)phosphine]palladium(0). The resulting solution was immediately spotted onto the glass plate (C1 or C2) obtained in (1) above, and this was kept at 60° C., 90% RH for one hour. Thus treated glass plate was then washed successively twice with a mixture of aqueous 0.1 wt. % SDS (sodium dodecyl sulfate) solution and aqueous 2×SSC solution (obtained by twice diluting standard sodium chloride-citrate buffer solution (SSC)), and once with the aqueous 0.2×SSC solution. Thus washed glass plate was placed in a solution of 0.1M succinic anhydride in acetonitrile (pH 10) for 1.5 hours, washed with distilled water, and then dried at room temperature, to obtain a glass plate (D1 or D2) on which the oligonucleotides were fixed.

The fluorescence strength of thus treated plate (D1 or D2) was measured using a fluorescence scanning apparatus. The fluorescence strength was 1,750 for D1 and 1,780 for D2, which were well higher than the background fluorescence strength. This means that the oligonucleotides are well fixed onto the glass plate.

EXAMPLE 2

Detection of Target Oligonucleotide (1) Preparation of DNA chip

A DNA chip, namely, glass plate (D3 or D4) on which the oligonucleotides were fixed was prepared in the same manner as in Example 1-(1) except for using the oligonucleotide having no fluorescent label.

(2) Detection of Target Oligonucleotide

A target oligonucleotide (GATCAGACACTTCACAGACTAG-5', 22-mers) having Cy5 (fluorescent label) at its 5'-terminal was dispersed in 20 µL of a hybridizing solution (mixture of 4×SSC and 10 wt. % SDS). The resulting solution was spotted onto the glass plate (D3 or D4) prepared in (1) above, and its spotted surface was covered with a covering glass. Thus covered chip was subjected to incubation at 60° C. for 20 hours in a moisture chamber. The incubated chip was washed successively with a mixture of 0.1 wt. % SDS and 2×SSC, a mixture of 0.1 wt. % SDS and 0.2×SSC, and an aqueous 0.2×SSC solution, centrifuged at 600 r.p.m. for 20 seconds, and dried at room temperature.

The fluorescence strength of thus treated glass plate (D3 or D4) was measured using a fluorescence scanning apparatus. The fluorescence strength was 688 for D3 and 710 for D4, which were well higher than the background fluorescence strength. This means that the target oligonucleotides are well fixed to the DNA chip having the complementary oligonucleotide probe.

What is claimed is:

1. An element comprising a solid carrier and a nucleotide derivative or analogue thereof selected from the group consisting of oligonucleotides, polynucleotides and peptide-nucleotides which are fixed to the solid carrier via covalent bonding, in which the covalent bonding is produced by a reaction between a first reactive group attached to the solid carrier and a second reactive group attached to the nucleotide derivative or analogue in the presence of a transition metal-containing catalyst, in which the first reactive group is selected from the group consisting of a residue of an alkylboronic acid, a residue of an alkenylboronic acid and a residue of an arylboronic acid and the second reactive group is selected from the group consisting of a residue of an alkenyl halide and an aryl halide, or in which the first reactive group is selected from the group consisting of a residue of an alkenyl halide and an aryl halide and the second reactive group is selected from the group consisting of a residue of an alkylboronic acid, a residue of an alkenylboronic acid and a residue of an arylboronic acid.

2. The element of claim 1, wherein the transition metal contained in the catalyst is selected from the group consisting of scandium, cobalt, nickel, copper, ruthenium, rhodium, palladium and lanthanids.

3. A method for preparing an element comprising a solid carrier and a nucleotide derivative or analogue thereof selected from the group consisting of oligonucleotides, polynucleotides and peptide-nucleotides fixed to the solid carrier via covalent bonding which comprises bringing in a liquid phase, the nucleotide derivative or analogue thereof having a reactive group adjacent and end thereof into contact with a solid carrier, in which the first reactive group is selected from the group consisting of a residue of an alkylboronic acid, a residue of an alkenylboronic acid and a residue of an arylboronic acid and the second reactive group is selected from the group consisting of a residue of an alkenyl halide and an aryl halide, or in which the first reactive group is selected from the group consisting of a residue of an alkenyl halide and an aryl halide and the second reactive group is selected from the group consisting of a residue of an alkylboronic acid, a residue of an alkenylboronic acid and a residue of an arylboronic acid.

4. The element of claim 1, wherein the transition metal-containing catalyst is a palladium-containing catalyst.

5. The method of claim 3, wherein the transition metal contained in the catalyst is selected from the group consisting of scandium, cobalt, nickel, copper, ruthenium, rhodium, palladium and lanthanids.

6. The method of claim 3, wherein the transition metal-containing catalyst is a palladium-containing catalyst.

7. An element comprising a solid carrier and a nucleotide derivative or analogue thereof selected selected from the group consisting of oligonucleotides, polynucleotides or peptide-nucleotides which are fixed to the solid carrier via covalent bonding, in which the covalent bonding is produced by a reaction between a first reactive group attached to the solid carrier and a second reactive group attached to the nucleotide derivative or analogue in the presence of a transition metal-containing catalyst, in which the first reactive group is selected from the group consisting a residue of an alkenyl halide or a residue of an aryl halide and the second reactive group is a residue of an alkyne compound, or in which the first reactive group is a residue of an alkyne compound and the second reactive group is selected from the group consisting of a residue of an alkenyl halide or a residue of an aryl halide.

8. The element of claim 7, wherein the transition metal contained in the catalyst is selected from the group consisting of scandium, cobalt, nickel, copper, ruthenium, rhodium, palladium and lanthanids.

9. The element of claim 7, wherien the transition metal-containing catalyst is a palladium-containing catalyst.

10. A method for preparing an element comprising a solid carrier and a nucleotide derivative or analogue thereof selected from the group consisting of oligonucleotides, polynucleotides or peptide-nucleotides fixed to the solid carrier via covalent bonding which comprises bringing in a liquid phase the nucleotide derivative or analogue having a first reactive group at one end thereof or its vicinity into contact with a solid carrier having thereon a second reactive group in the presence of a transition metal-containing catalyst, in which the first reactive group in selected from the group consisting of a residue of an alkenyl halide or a residue of an aryl halide and the second reactive group is a residue of an alkyne compound, or in which the first reactive group is a residue to an alkyne compound and the second reactive group is selected from the group consisting of a residue of an alkenyl halide or a residue of an aryl halide.

11. The method of claim 10, wherein the transition metal contained in the catalyst is selected from the group consisting of scandium, cobalt, nickel, copper, rutherium, rhodium, palladium and lanthanids.

12. The method of claim 10, wherein the transition metal-containing catalyst is a palladium-containing catalyst.

* * * * *